United States Patent
Maas et al.

(10) Patent No.: US 6,693,278 B2
(45) Date of Patent: Feb. 17, 2004

(54) PARTICLE-OPTICAL INSPECTION DEVICE ESPECIALLY FOR SEMICONDUCTOR WAFERS

(75) Inventors: Diederik Jan Maas, Eindhoven (NL); Jan Martijn Krans, Eindhoven (NL)

(73) Assignee: FEI Company, Hillsboro, OR (US)

( * ) Notice: Subject to any disclaimer, the term of this patent is extended or adjusted under 35 U.S.C. 154(b) by 30 days.

(21) Appl. No.: 10/024,762

(22) Filed: Dec. 20, 2001

(65) Prior Publication Data

US 2002/0079447 A1 Jun. 27, 2002

(30) Foreign Application Priority Data

Dec. 22, 2000 (EP) .............................................. 00204808

(51) Int. Cl.⁷ .......................... G01N 23/00; G21K 7/00; G02B 21/00; G06K 9/00
(52) U.S. Cl. ....................... 250/310; 250/306; 250/307; 250/309; 250/311; 359/368; 382/147; 382/149
(58) Field of Search ................................ 250/306, 310, 250/311, 309, 492.22, 307; 359/368; 382/147, 149

(56) References Cited

U.S. PATENT DOCUMENTS

| | | | | |
|---|---|---|---|---|
| 4,338,028 A | * | 7/1982 | Tailleur et al. ........... 356/239.4 |
| 4,417,203 A | * | 11/1983 | Pfeiffer et al. ............... 324/501 |
| 4,812,651 A | * | 3/1989 | Feuerbaum et al. ......... 250/310 |
| 4,851,768 A | * | 7/1989 | Yoshizawa et al. ......... 324/751 |
| 4,983,850 A | * | 1/1991 | Tsukakoshi et al. ..... 250/492.3 |
| 5,399,860 A | * | 3/1995 | Miyoshi et al. ............. 250/310 |
| 5,578,821 A | * | 11/1996 | Meisberger et al. ........ 250/310 |
| 5,641,960 A | | 6/1997 | Okubo et al. ................ 250/310 |
| 6,043,932 A | * | 3/2000 | Kusunose .................... 359/368 |
| 6,195,202 B1 | * | 2/2001 | Kusunose .................... 359/368 |
| 6,285,783 B1 | * | 9/2001 | Isomura et al. ............. 382/147 |
| 6,528,818 B1 | * | 3/2003 | Satya et al. .................... 257/48 |
| 6,587,581 B1 | * | 7/2003 | Matsuyama et al. ........ 382/149 |

FOREIGN PATENT DOCUMENTS

| | | | |
|---|---|---|---|
| WO | WO9950651 | 7/1999 | ......... G01N/23/225 |
| WO | WO9934397 | 8/1999 | ............ H01J/37/28 |

OTHER PUBLICATIONS

Patent Abstracts Of Japan, Tanabe Yoshikazu, "Defect Inspector," Publication No. 59006537, Jan. 13, 1984, Application No. 57115432, Jul. 5, 1982.

\* cited by examiner

*Primary Examiner*—John R. Lee
*Assistant Examiner*—Mary El-Shammaa
(74) *Attorney, Agent, or Firm*—Michael O. Scheinberg; Erik Nordstrom

(57) ABSTRACT

In the production of semiconductors it is necessary to inspect circuit patterns on wafers. In circuits having very small details (for example, 40 nm), inspection can be carried out by means of electron beam columns, a plurality of wafers then being inspected at the same time and the signals being compared on-line. In an inspection apparatus in accordance with the invention more beam columns 1 to 7 are provided for every wafer A, B, C in order to obtain a high feed-through rate. The inspection is carried out by way of an x-y scan and the wafers are fed through according to a rectilinear movement, thus providing the possibility of scanning only the Care Area Fraction of the wafers, resulting in a high feed-through rate for the wafers in the inspection apparatus.

18 Claims, 3 Drawing Sheets

PARTICLE-OPTICAL INSPECTION DEVICE ESPECIALLY FOR SEMICONDUCTOR WAFERS

CROSS-REFERENCE TO RELATED APPLICATIONS

This application claims the benefit under 35 USC 119 of earlier filed EP Pat. App. 00204808.0, filed on Dec. 22, 2000.

STATEMENT REGARDING FEDERALLY PROMISED RESEARCH OR DEVELOPMENT

Not Applicable

INCORPORATION BY REFERENCE OF MATERIALS SUBMITTED ON A COMPACT DIS

Not Applicable

BACKGROUND OF THE INVENTION

The invention relates to a device for the inspection of patterns on objects, which device is provided with:

a carrier unit for carrying the objects during the inspection, for each object an inspection unit that includes at least one particle-optical column for scanning the pattern to be inspected on the associated object, a comparison circuit for comparing the scan signals that are produced by the particle-optical column in a first inspection unit and by the particle-optical column in a second inspection unit, which device is arranged for the simultaneous inspection of corresponding patterns on a plurality of objects.

A device of the kind set forth is known from U.S. Pat. No. 5,641,960.

In the semiconductor industry there is a need for equipment that is suitable for the inspection of patterns written on wafers, for example, for the detection of defects arising during the manufacturing process. Such defects may be the cause of malfunctioning of the manufactured integrated circuits (ICs) so that they have to be rejected. As the smallest critical dimensions of the ICs become smaller and smaller, it is necessary to have inspection equipment available that is still capable of suitably discriminating such small details. The contemporary dimensions of the order of magnitude of 200 nm of the smallest details necessitate a resolution of the inspection equipment of approximately 50 nm; it is generally expected that this resolution will have to be improved even further in the near future.

Optical equipment that operates in the field of the visible light is no longer adequate to achieve such a high resolution. The use of particle-optical equipment, notably scanning electron microscopes (SEMs), however, enables suitable observation of such small details.

The cited United States patent describes a device for the inspection of patterns on objects, said device being arranged to inspect circuits on semiconductor wafers. The known device is provided with a carrier unit with a carrier or stage for the wafers that rotates during the acquisition of the signals that are required for the inspection. For each wafer there is provided an inspection unit in the form of an electron optical SEM column that carries out the wafer inspection. The entire wafer surface can be accessed for inspection by the SEM columns in that the carrier rotates relative to the columns and in that during the inspection the columns are displaced in the radial direction relative to the axis of rotation of the carrier. Because the described known device is arranged for the simultaneous inspection of corresponding patterns on different wafers, the scan signals produced by the particle-optical columns can be compared by a comparison circuit, so that the existence of a defect can be decided upon when a difference between these signals is detected. This comparison can be performed in "real time", so that it is not necessary to form and maintain very large data bases with which the signals have to be compared and that it is not necessary either to carry out time-consuming digital comparison operations between the instantaneous scan signals and the stored data.

Because the known device is provided with only one column for each wafer, inspection in this device can take place at a comparatively low feed-through rate only. This can be demonstrated as follows. As the details of the patterns to be inspected become smaller, the number of details to be inspected for each wafer increases, that is, by the square of the detail reduction (the wafer dimensions remaining the same). As a result, inspection of the entire wafer surface is dispensed with and only the areas within the patterns in which the smallest detail size occurs are inspected, that is, the so-called Care Areas. The fraction of the pattern in which such Care Areas are situated is known as the Care Area Fraction (CAF) that typically has a value of the order of magnitude of 1%. The feed-through rate during inspection can be considerably increased by inspecting only the CAF; however, in order to make wafer inspection in future keep pace with the production rate of the wafers (which is necessary for on-line inspection of the wafers), the CAF must be strongly reduced, so that parts of the patterns that are prone to defects would have to be skipped; of course, such a development is undesirable.

The inspection of the wafers in the known device is performed by making the wafer rotate relative to the inspecting column. During this rotational displacement the passing wafer is irradiated by an electron beam that is produced by the column and is stationary relative to the column during the execution of the inspection scan. The area of the wafer that is inspected per revolution of the carrier is thus shaped as a circular path; if a larger area is to be inspected, for example, an area having a rectangular shape, such an area will have to be composed from a number of adjoining circular paths. This means that it is still possible to select a number of care areas for inspection, but also that the surface area of the circular paths that are situated between the care areas must also be covered. Consequently, the scan time cannot be reduced by skipping such intermediate areas.

This method of scanning also has the drawback that the factor limiting the speed of rotation (for example, the processing speed of the electronic circuitry used for the data comparison) is based on the highest speed that occurs, that is, the speed of the areas at the outer periphery of the circle of rotation, that is, the location where the maximum radial position of the columns is situated. All areas to be inspected within this maximum circle of rotation, therefore, have a non-optimum speed, so that the device is overproportioned for the vast majority of the areas to be inspected.

BRIEF SUMMARY OF THE INVENTION

It is an object of the invention to provide a solution to the problem of maintaining the feed-through rate during on-line inspection of semiconductor wafers with increasingly greater circuit densities. To this end, the device in accordance with the invention is characterized in that the particle-optical columns are arranged to carry out an x-y scan of the pattern on the objects by x-y deflection of the particle beam that is produced by the relevant particle-optical column, and that the carrier unit is arranged to realize a rectilinear translatory feed-through direction for the objects. In the device in accordance with the invention the objects to be inspected (the wafers) are arranged underneath the inspection column in such a manner that they are oriented on the carrier in the direction perpendicular to the feed-through direction of the carrier (for example, to be referred to hereinafter as the x direction) in such a manner that they occupy the desired position relative to the column. In the (rectilinear translatory) feed-through direction (for example, referred to as the y direction) wafers are arranged in the desired location underneath the inspection column in such a manner that they occupy the desired position relative to the column in said direction as a result of adjustment of the feed-through distance. The scanning of the desired care areas takes place after such positioning in that the electron beam that is produced by the column is scanned across the area to be inspected in the customary manner. Because this scan is executed under the control of an electron beam, such scanning requires a substantially smaller amount of time than the physical rotary displacement of the objects relative to the column.

An embodiment of the device in accordance with the invention is arranged to superpose on at least one of the scan signals a periodic signal that varies linearly in time and whose period is greater than that of the relevant scan signal. During the scanning of an area to be inspected by means of a SEM, the electron beam is deflected in two mutually perpendicular directions, that is, the x direction and the y direction. This deflection is realized by applying periodic deflection signals that vary in time to the SEM. When a further linear signal is superposed on one or on both scan signals, not only the scan motion for the inspection is realized but also a linear motion of the entire inspection area. As a result of this step, the object to be inspected can be displaced relative to the column during the scan, so that the scan area can be made to move along with the moving object. The objects can thus be fed through very gradually and without abrupt changes; this may be an advantage especially in the case of wafer inspection.

A preferred embodiment of the device in accordance with the invention is constructed in such a manner that each of the inspection units is provided with an array of at least two particle-optical columns and that the particle-optical columns occupy a fixed position relative to one another.

Because each inspection unit includes a plurality of particle-optical columns, a higher feed-through rate can in principle be achieved. However, such a higher rate is possible only if corresponding columns within different inspection units can simultaneously inspect corresponding areas of different wafers. Generally speaking, the distance between two corresponding parts of the pattern (that is, areas of a similar structure within different patterns) on a wafer will not be the same as the distance between two corresponding columns. In that case real-time pattern comparison will be impossible. It could be deliberated to adapt the pitch of the position of the columns to the pitch of the CAFs to be inspected (that is, to make the positions of the columns within an inspection unit variable), but the device would then become much more complex than in the case of a fixed relative position of the columns.

Within the limits that are imposed by the amount of space available, however, an arbitrarily large number of particle-optical columns can be chosen for each inspection unit, that is, for each wafer, so that a gain in feed-through rate can still be obtained as will be illustrated on the basis of the following numerical example. By way of example it is assumed that the CAF amounts to 1%, that seven columns (1 to 7) are provided for each inspection unit, and that three wafers are inspected simultaneously; this means that there are three inspection units (A, B, C). The wafers to be inspected can be supplied on the carrier unit in such a manner and the columns can be arranged at such a distance from one another that a corresponding area of each wafer is inspected. Each time one column of each inspection unit is then in operation, for example, the columns A1, B1 and C1. In this example, therefore, three out of 21 columns are simultaneously in operation. However, it is now possible to increase the CAF considerably by choosing the areas to be inspected to be such that also the columns A2, B2 and C2 are simultaneously in operation, that is, also simultaneously with A1, B1 and C1. In the latter example six out of 21 columns are then simultaneously in operation. The same is also possible for the other columns, so that even more columns are simultaneously in operation. The feed-through rate can thus be increased without it being necessary to reduce the CAF, or the CAF can be increased without reducing the feed-through rate.

Because the columns do not move at the time of execution of the inspection scan, there will be no uncertainty as regards their position relative to one another and the limit of the resolution that can be achieved during the inspection will be determined only by the resolution of the columns themselves; in accordance with the present state of the art, this resolution may be of the order of magnitude of a few nanometers.

A further preferred embodiment of the device in accordance with the invention is provided with at least three inspection units. This embodiment offers the advantage that during the comparison of the scan signals a simple majority decision can be taken so as to decide which of the three signals is deviant, that is, to decide in which wafer the defect occurs.

The particle-optical columns in a further embodiment of the device in accordance with the invention columns are arranged along one line and the carrier unit is arranged to realize a feed-through direction for the objects that extends perpendicularly to the direction of said line. Each point of each wafer can thus be readily reached by the columns for inspection and the positioning accuracy of the wafers in the feed-through direction is maximum in the case of a rectilinear feed-through. When the columns are arranged along one line, the wafers are also arranged along one line, so that the positioning accuracy of the wafers is maximum in the line direction.

The particle-optical columns in another embodiment yet of the device in accordance with the invention are constructed as electron optical columns and the optical elements in the electron optical columns are constructed as electrostatic elements. For miniaturization of a SEM it is advantageous to utilize electrostatic optical elements, such as the beam deflection electrodes or the objective, because they can be constructed so as to be smaller than magnetic elements. This is due to the absence of the need for cooling means (notably cooling ducts for the lens coil), and due to the fact that the magnetic (iron) circuit of the lens must have a given minimum volume in order to prevent magnetic saturation. Moreover, because of the requirements that are imposed nowadays in respect of high vacuum in the sample space, electrostatic electrodes (being constructed as smooth metal surfaces) are more attractive than the surfaces of a magnetic lens since the surfaces thereof are often provided with coils, wires and/or vacuum rings.

BRIEF DESCRIPTION OF THE SEVERAL VIEWS OF THE DRAWING(S)

The invention will be described in detail hereinafter with reference to the drawing in which corresponding elements are denoted by corresponding reference numerals. Therein:

DETAILED DESCRIPTION OF THE INVENTION

Figure 1:
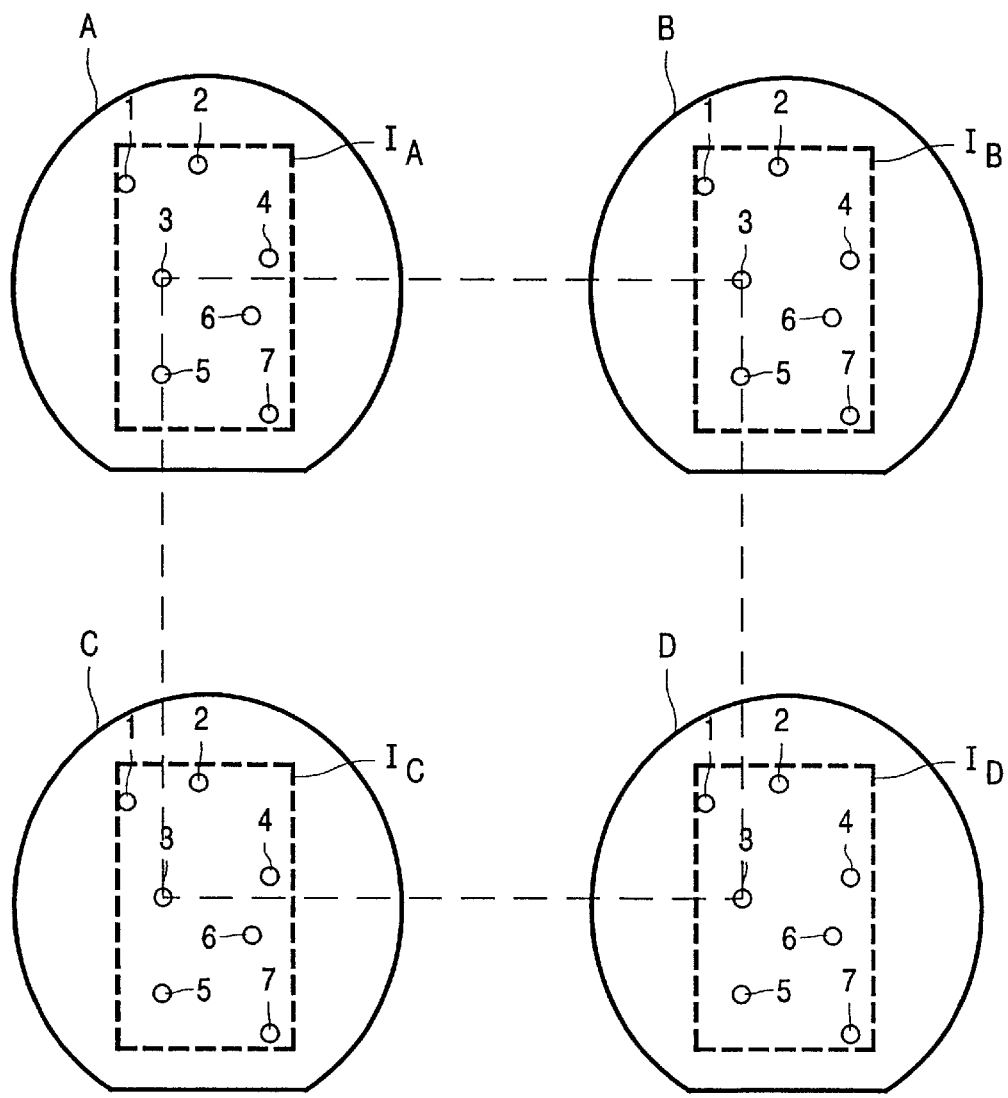
FIG. 1 is a diagrammatic view of a number of wafers and an array of particle-optical columns for each wafer.

In order to illustrate the idea of the invention FIG. 1 shows a number of wafers A to D and an inspection unit $I_A$–$I_D$ for each wafer, each of said inspection units I being provided with seven particle-optical columns 1 to 7 for scanning the pattern to be inspected on the associated wafer. The particle-optical columns are constructed as electron optical columns. The electron optical columns 1 to 7 are arranged in the same way in each inspection unit and the inspection units $I_A$–$I_D$ are also arranged in the same way relative to the wafers A to D; this means that, for example, the column 1 in the inspection unit $I_A$ occupies the same position relative to the wafer A as the column 1 in the inspection unit IB relative to the wafer B.

The electron optical columns 1 to 7 may occupy a fixed position relative to the wafers A to D during the execution of an inspection scan, the wafers then being stationary relative to the complete inspection apparatus in which the inspection is carried out. This prevents the occurrence of mechanical vibrations that would degrade the resolution of the inspection apparatus during the inspection scan. Because the columns in this case do not move during the execution of the inspection scan (and neither do the patterns to be inspected), there will be no uncertainty as regards the position of the columns relative to these patterns, so that the limit of the resolution that can be achieved upon inspection is governed exclusively by the resolution of the columns themselves; in accordance with the present state of the art said resolution may be of the order of magnitude of only a few nanometers. However, it is also possible for the wafers to be transported along the columns at a uniform speed, the image area of the column then being moved along with the wafers by way of suitable control of the beam deflection signals. The choice for a stationary or a moving scan is dependent on the other circumstances in which the inspection scan takes place and on the requirements imposed as regards resolution.

The wafers to be inspected can be supplied in such a manner and the columns can be arranged at such a distance from one another that a corresponding area of each wafer is inspected; this means that in the case of non-defective patterns each column picks up exactly the same image and hence produces the same detection signal. If the mechanical alignment of the columns relative to the patterns to be inspected is not completely perfect, the necessary small correction for this deviation can be realized by applying a fixed DC bias to the deflection electrodes of the columns (see FIG. 3), so that in the absence of a scan signal the primary electron beams are all incident at exactly the same point in each of the patterns to be inspected. An alternative correction method consists in compensating for the deviation from the perfect mechanical alignment by introducing a time delay in one or more detection signals upon comparison; this is because the (slight) deviation from the ideal alignment becomes manifest as a time shift in the detection signal because the image of the pattern to be inspected is picked up by scanning.

Figure 2:
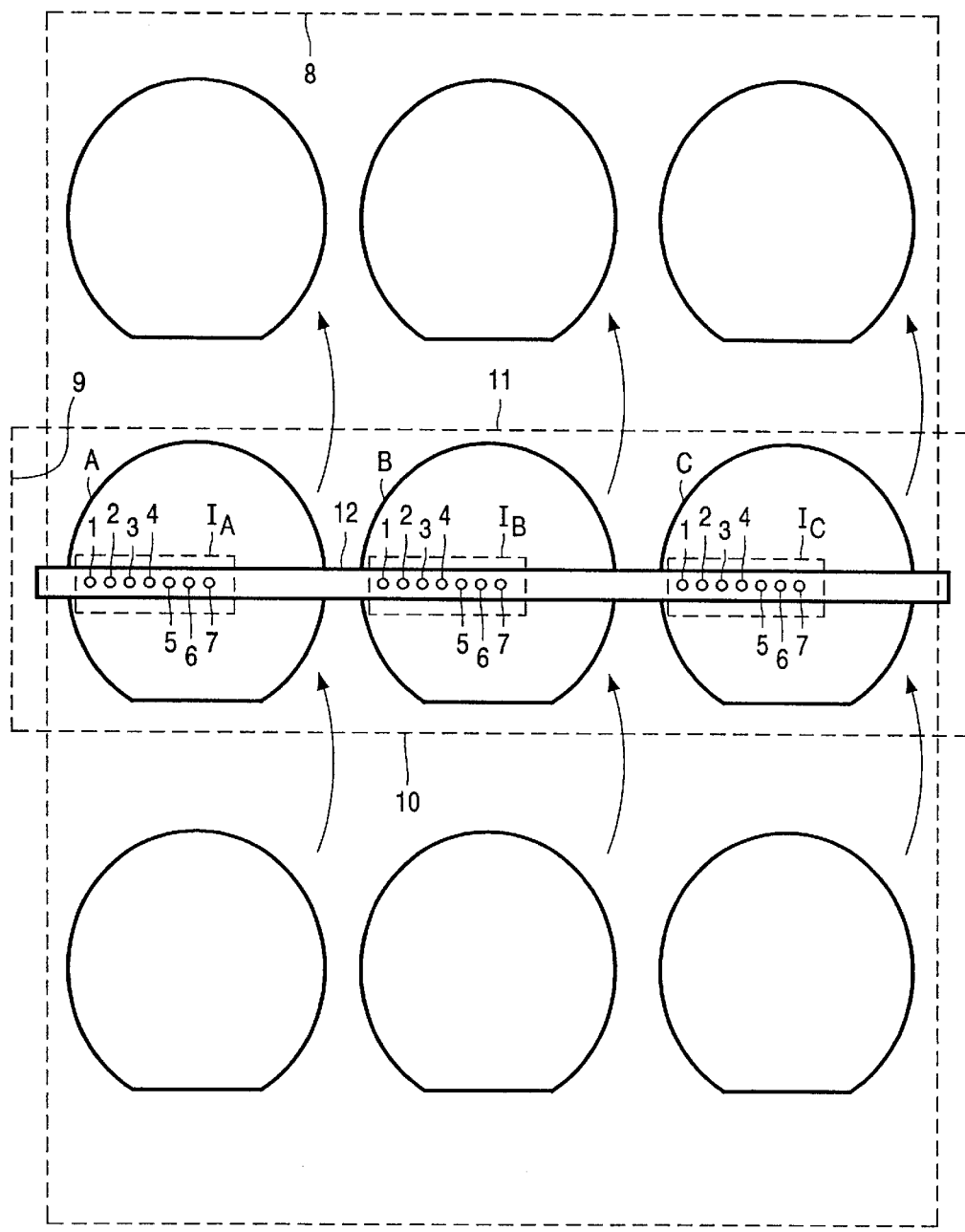
FIG. 2 is a diagrammatic view of a preferred embodiment of the device in accordance with the invention with three rows of wafers and a linear array of particle-optical columns for each wafer.

FIG. 2 is a diagrammatic representation of a preferred embodiment of the invention with three rows of wafers and a respective linear array of particle-optical columns for each wafer. The set of wafers to be inspected in this Figure consists of three wafers A, B and C that are fed to and fro an inspection space 9 on a carrier unit 8. The actual inspection of the wafers takes place in said inspection space. Because the inspection of the wafers is performed by means of electron beams, said inspection space is evacuated; the transport of the wafers into and out of this space takes place via vacuum or load locks 10 and 11.

During the actual inspection the inspection space 9 accommodates three wafers A, B and C and an inspection unit $I_A$, $I_B$ and $I_C$ for each wafer; each of said inspection units I is provided with seven electron optical columns 1 to 7 that serve to scan the pattern to be inspected on the associated wafer and all units are arranged on a frame 12. The electron optical columns 1 to 7 in each inspection unit are arranged along a straight line in the same way and the inspection units $I_A$ to ID are also arranged in the same way relative to the wafers A to C; this means that, for example, the column 1 in the inspection unit $I_A$ occupies the same position relative to the wafer A as the column 1 in the inspection unit $I_B$ relative to the wafer B. The scan signals that are produced by the corresponding columns in the various inspection units are applied to a comparison circuit (not shown in the Figure) in which said scan signals are compared. A comparison circuit of this kind may be formed, for example, by a differential amplifier that is configured in such a manner that it produces an output signal zero when the input signals are equal whereas it produces an output signal other than zero when the input signals applied thereto exhibit a difference that exceeds a given threshold value.

Figure 3:
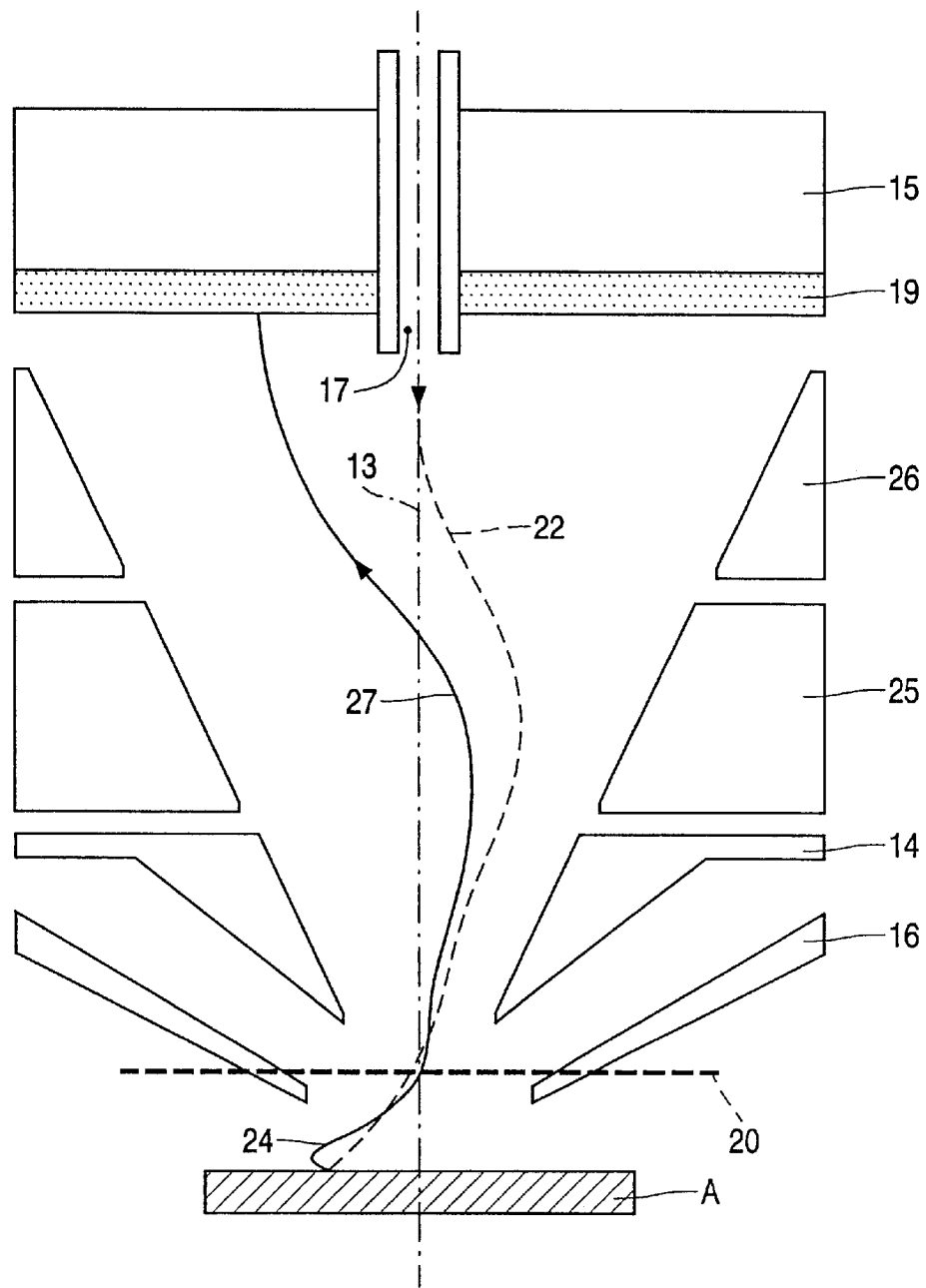
FIG. 3 shows a particle-optical column that is suitable for use in accordance with the invention.

FIG. 3 shows a relevant part of an electron optical column for use in accordance with the invention, that is, in the form of a scanning electron microscope (SEM). The electron source and all other elements that form part of the electron optical column and are intended to accelerate and control the primary beam have been omitted in as far as they are not relevant to the invention. The primary beam 22 travels along the optical axis 13 of the SEM. During its travel the primary beam successively passes a detector crystal 15, via a bore 17, an electrostatic acceleration electrode 19, a first electrical deflection electrode 26, a second electrical deflection electrode 25, a first electrostatic electrode 14 that forms part of the objective and a second electrostatic electrode 16 that also forms part of the objective. Finally, the electrons of the primary beam reach a wafer to be inspected, for example the wafer A as shown in the FIGS. 1 and 2.

The electrostatic acceleration electrode 19 forms part of the electrode system 19, 14, 16, the electrodes 14 and 16 of which form the objective of the column that serves to focus the primary beam. The electrode 19 is shaped as a flat plate that is provided with a bore 17 for the primary beam and is deposited on the scintillation crystal 15 in the form of a conductive oxide, for example indium oxide and/or tin oxide. The electrode 19 can be adjusted to a desired voltage of, for example 9 kV.

The first electrical deflection electrode 26 and the second electrical deflection electrode 25 form part of a beam deflection system for deflecting the primary beam. Each of these two electrodes is constructed as a tubular portion that has an external shape in the form of a straight circular cylinder and an internal shape in the form of a cone that is tapered in the direction of the beam. Each of the electrodes 26 and 25 is subdivided into four equal parts by way of two saw cuts in mutually perpendicular planes through the optical axis, so that each of the electrodes 26 and 25 is capable of producing electrical dipole fields in the x direction as well as the y direction when suitable voltage differences are applied between the parts, with the result that the primary beam can be scanned across the wafer A and the path of the secondary electrons that travel in the direction of the detector crystal 15 can be influenced.

The first electrode 14 and the second electrodes 16 constitute the electrode system which forms the objective of the SEM. A dashed line 20 in the Figure also indicates the region in which the lens effect that is due to the electrical objective field (that is, the paraxial center of the objective) can be assumed to be localized. The objective 14, 16 focuses the primary beam in such a manner that the electron source is imaged on the wafer with a reduction that is generally very large.

The Figure shows the course of some electron paths in the particle-optical instrument. The primary beam 22 that enters the assembly formed by the detector, the deflection electrodes and the objective (which beam is only diagrammatically represented by a dashed line in this Figure) initially travels along the optical axis 13. Under the influence of the electrical deflection field that is generated by the electrode 26, the beam is deflected away from the axis, after which it is deflected towards the axis again under the influence of the opposed deflection field that is generated by the electrode 25. As a result, the primary beam intersects the optical axis far below the deflection electrodes 26 and 25. As a result of the arrangement of the beam deflection system and the fact that this system operates with two opposed fields, it is achieved that the tilting point is situated in the central plane 20 of the objective, so that a large field of view and a minimum imaging error are obtained, irrespective of the magnitude of the scanning motion of the primary beam. This phenomenon can be clearly observed in the Figure which shows that, after deflection by the deflection fields, the primary beam intersects the optical axis 13 in the central plane 20.

The incidence of the primary beam 22 on the wafer A releases secondary electrons from the sample; such secondary electrons travel upwards under the influence of the electrical field of the objective, of the deflection system and of the detector voltage. The Figure shows a path 24 of such a secondary electron. The secondary electron is pulled into the bore of the objective, after which it becomes subject to the influence of the deflection fields. The effect of the electrical deflection fields is represented by the path 27 in the Figure.

The beam of secondary electrons 27 produces an electrical signal in the detector 15, which signal is applied to the comparison circuit that is not shown in the Figures.

What is claimed is:

1. A device for the inspection of patterns on objects, which device is provided with:
    a carrier unit (8) for carrying the objects (A, B, C) during the inspection,
    for each object an inspection unit (IA, IB, IC) that includes at least one particle-optical column for scanning the pattern to be inspected on the associated object,
    a comparison circuit for comparing the scan signals that are produced by the particle-optical column in a first inspection unit (A) and by the particle-optical column in a second inspection unit (B), which device is arranged for the simultaneous inspection of corresponding patterns on a plurality of objects, characterized in that
    the particle-optical columns (1 to 7) are arranged to carry out an x-y scan of the pattern on the objects by x-y deflection of the particle beam (22) that is produced by the relevant particle-optical column, and that
    the carrier unit is arranged to realize a rectilinear translatory feed-through direction for the objects.

2. A device as claimed in claim 1, which device is arranged to superpose on the scan signal that has the largest period a periodic signal that varies linearly in time and whose period is greater than that of the relevant scan signal.

3. A device as claimed in claim 1, in which each of the inspection units is provided with an array of at least two particle-optical columns and in which the particle-optical columns in each array occupy a fixed position relative to one another.

4. A device as claimed in claim 3, which device is provided with at least three inspection units.

5. A device as claimed in claim 3, in which the particle-optical columns are arranged along one line and in which the carrier unit is arranged to realize a feed-through direction for the objects that extends perpendicularly to the direction of said line.

6. A device as claimed in claim 1, in which the particle-optical columns are constructed as electron optical columns and in which the optical elements in the electron optical columns are constructed as electrostatic elements.

7. A device for the inspection of an object set having two or more objects that each have a corresponding pattern, wherein the corresponding patterns in the object set correspond to each other, the device comprising:
    a plurality of inspection units each associated with an object in the object set, each inspection unit having a particle-optical column for performing an X-Y scan of at least a portion of the corresponding pattern on its associated object and outputting a scan image signal for the pattern portion being scanned;
    at least one carrier unit for carrying a plurality of the object sets in order for the objects in each set to be simultaneously inspected, the at least one carrier unit being configured to realize a rectilinear translatory feed-through displacement of the objects in each set relative to the inspection units; and
    a comparison circuit for comparing the outputted scan image signals in order to compare corresponding pattern portions with one another to determine if any pattern portion in the set being inspected is different from other pattern portions in the set.

8. A device as claimed in claim 7, wherein the at least one carrier unit moves the objects while they are scanned, the device being arranged to superpose on the scan signals from each particle-optical device a periodic signal to cause its scan area to move with the object it is scanning.

9. A device as claimed in claim 7, in which each of the inspection units is provided with an array of at least two particle-optical columns and in which the particle-optical columns in each array occupy a fixed position relative to one another.

10. A device as claimed in claim 9, which device is provided with at least three inspection units.

11. A device as claimed in claim 9, in which the particle-optical columns are arranged along one line and in which the at least one carrier unit is arranged to realize a feed-through direction for the objects that extends perpendicularly to the direction of said line.

12. A device as claimed in claim 7, in which the particle-optical columns are constructed as electron optical columns and in which the optical elements in the electron optical columns are constructed as electrostatic elements.

13. A device for simultaneously inspecting corresponding care areas on first and second wafers, the device comprising:

first and second inspection units respectively associated with the first and second wafers, said first and second inspection units each having a particle-optical column for scanning at least a portion of the corresponding care area on the wafer associated with its inspection unit and outputting a scan image signal indicative of the care area image portion being scanned;

at least one carrier unit for carrying multiple sets of the first and second wafers in order to linearly feed the wafer sets to the inspection units for simultaneous inspection of first and second corresponding care area portions in each wafer set; and a comparison circuit coupled to the particle-optical columns for comparing the outputted first and second scan image signals in order to determine if the first and second corresponding care areas in the set being inspected are different.

14. The device of claim 13, wherein the at least one carrier unit is configured to serially feed the wafer sets, one at a time, to the inspection units, halted while a set is being inspected, and then proceeded to present the next wafer set to the inspection units for inspection.

15. The device of claim 13, wherein the at least one carrier unit continually feeds the wafer sets past the inspection units, and a signal is superposed onto a deflection signal for each particle-optical column so that scan areas for the particle-optical columns move in synchronicity with the carrier unit and thus with a wafer set being scanned.

16. A method for inspecting a plurality of objects with like portions, comprising:

providing two or more inspection units, each inspection unit having at least one particle-optical device;

simultaneously presenting to each inspection unit one of the plurality of objects;

with the at least one particle-optical device in each inspection unit, scanning the like portion of the object presented to the inspection unit; and comparing the scanned like portions to determine if any are different from the others.

17. The method of claim 16, further comprising continually passing the presented objects past the inspection units as they are being scanned and compared with one another.

18. A method of identifying defective wafers from a plurality of wafers having corresponding patterns, comprising:

(a) simultaneously scanning the corresponding patterns from two or more of the plurality of wafers;

(b) for each pattern being scanned, generating a scan signal indicative of the pattern; and (c) comparing the scan signals to determine if any signal is different from the others thereby indicating that at least one of the simultaneously scanned patterns is incorrect and its wafer is defective.

* * * * *